(12) United States Patent
Levy et al.

(10) Patent No.: US 6,395,253 B2
(45) Date of Patent: *May 28, 2002

(54) MICROSPHERES CONTAINING CONDENSED POLYANIONIC BIOACTIVE AGENTS AND METHODS FOR THEIR PRODUCTION

(75) Inventors: Robert J. Levy, Merion, PA (US); Vinod Labhasetwar, Omaha, NE (US); Hagit Cohen, Jerusalem (IL)

(73) Assignee: The Regents of the University of Michigan, Ann Arbor, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/065,892

(22) Filed: Apr. 23, 1998

(51) Int. Cl.$^7$ .............................................. A61K 51/00
(52) U.S. Cl. .................... 424/1.25; 424/497; 424/9.322; 536/23.5
(58) Field of Search ................. 427/2.3, 213; 424/85.2, 424/426, 493, 1.25, 497; 435/69.1, 320.1; 514/12, 44; 525/54.2; 604/28, 96, 509; 536/23.5

(56) References Cited

U.S. PATENT DOCUMENTS

| | | | |
|---|---|---|---|
| 4,272,398 A | 6/1981 | Jaffe | 427/213 |
| 5,298,422 A | 3/1994 | Schwartz et al. | 435/370.1 |
| 5,304,121 A | 4/1994 | Sahatjian | 604/509 |
| 5,324,775 A | 6/1994 | Rhee et al. | 525/54.2 |
| 5,460,831 A | 10/1995 | Kossovsky et al. | 424/493 |
| 5,464,650 A | 11/1995 | Berg et al. | 427/2.3 |
| 5,470,829 A | 11/1995 | Prissell et al. | 514/12 |
| 5,478,564 A | 12/1995 | Wantier et al. | 424/426 |
| 5,480,656 A | 1/1996 | Okada et al. | 424/493 |
| 5,545,135 A | 8/1996 | Iacob et al. | 604/96 |
| 5,580,859 A | 12/1996 | Felgner et al. | 514/44 |
| 5,593,974 A | 1/1997 | Rosenberg et al. | 514/44 |
| 5,674,192 A | 10/1997 | Sahatjian et al. | 604/28 |
| 5,674,703 A | 10/1997 | Woo et al. | 435/69.1 |
| 5,693,622 A | 12/1997 | Wolff et al. | 514/44 |
| 5,698,531 A | 12/1997 | Nabel et al. | 514/44 |
| 5,707,969 A | 1/1998 | Nabel et al. | 514/44 |
| 5,723,119 A | 3/1998 | Schwartz et al. | 424/85.2 |
| 5,770,580 A | 6/1998 | Ledley et al. | 514/44 |

FOREIGN PATENT DOCUMENTS

| | | | |
|---|---|---|---|
| EP | 190833 | 8/1995 | |
| WO | WO 90/11092 | 10/1990 | |
| WO | WO 93/21969 | 11/1993 | |
| WO | WO 94/23738 | * 10/1994 | 514/44 |
| WO | WO 95/24929 | 9/1995 | |
| WO | WO 96/20698 | * 7/1996 | |
| WO | WO 97/38729 | 10/1997 | |
| WO | WO 97/47254 | 12/1997 | |
| WO | WO 98/19711 | 5/1998 | |

OTHER PUBLICATIONS

Uchida et. al.; Preparation and characterization of polylactic acid microspheres containing water–soluble dyes using a novel w/o/w emulsion solvent evaporation method, 1996, J. Microencapsulation vol. 13: 219–228.*

Uchida et. al.; Optimization of Preparative Conditions for Polylactide (PLA) Microspheres Containing Ovalbumin, 1995, Chem. Pharm. Bull. 43(9): 1569–1573.*

GenBank protein database Accession No. AAA48998, 1993.*

Cheng et al. In vivo and in vitro gene transfer and expression in rat intestinal epithelial cells by E1–deleted adenoviral vector. Human Gene Therapy 8: 755–764, especially abstract, Apr. 1997.*

Eldridge et al. Biodegradable microspheres: vaccine delicery system for oral immunization. Curr. Top. Microbiol. Immunol. 146: 59–66, abstract only, 1989.*

Allémann et al., 1992, "Preparation of aqueous polymeric nanodispersions by a reversible salting–out process: influence of process parameters on particle size," *Intl. J. Pharmaceutics* 87:247–253.

Fasbender et al., 1996, "Comlexes of Adenovirus with Polycationic Polymers and Cationic Lipids Increase the Efficiency of Gne Transfer in Vitro and in Vivo," *J. Biol. Chem.* 272:6479–6489.

Gottschalk et al., 1996, "A novel DNA–peptide complex for efficient gene transfer and expression in mammalian cells," *Gene Therapy* 3:448–457.

Katayose and Kataoka, 1997, "Water–Soluble Polyion Complex Associates of DNA and Poly(ethylene glycol)–Poly(L–lysine) Block Copolymer," *Bioconjugate Chem.* 8:702–707.

Laemmli, 1975, "Characterization of DNA condensates induced by poly(ethylene oxide) and polylysine," *Proc. Natl. Acad. Sci. USA* 72:4288–4292.

Lasic, 1997, *Liposomes in Gene Delivery*, CRC Press, Boca Raton, Florida, 33–37,56–61.

Ledley et al., 1987, "Somatic gene therapy for human disease: Background and prospects. Part I," *J. Pediatrics* 110:1–8.

Maruyama et al., 1997, "Nanoparticle DNA Carrier with Poly(L–lysine) Grafted Polysaccharide Copolymer and Poly(D,L–lactic acid)," *Bioconjugate Chem.* 8:735–742.

Nicolau et al., 1983, "In vivo expression of rat insulin after intravenous administration of the liposome–entrapped gene for rat insulin I," *Proc. Natl. Acad. Sci. USA* 80:1068–1072.

(List continued on next page.)

*Primary Examiner*—James Ketter
*Assistant Examiner*—Richard Schnizer
(74) *Attorney, Agent, or Firm*—Pennie & Edmonds LLP

(57) ABSTRACT

The invention describes improved methods for incorporating nucleic acids into polymeric microspheres and/or nanospheres through the use of a condensing agent.

18 Claims, No Drawings

OTHER PUBLICATIONS

Sosnowski et al., 1996, "Targeting DNA to Cells with Basic Fibroblast Growth Factor (FGF2)," *J. Biol. Chem.* 271:33647–33653.

Wadhwa et al., 1995, "Targeted Gene Delivery with a Low Molecular Weight Glycopeptide Carrier," *Bioconjugate Chem.* 6:283–291.

Wasan et al., 1996, "Plasmid DNA Is Protected against Ultrasonic Cavitation–Induced Damage When Complexed to Cationic Liposomes," *Journal of Pharmaceutical Sciences* 85:427–433.

Wolfert et al., 1996, "Characterization of Vectors for Gene Therapy Formed by Self–Assembly of DNA with Synthetic Block Co–Polymers," *Human Gene Therapy* 7:2123–2133.

Wolfert & Seymour, 1996, "Atomic force microscopic analysis of the influence of the molecular weight of poly(L)lysine on the size of polyelectrolyte complexes formed wtih DNA," *Gene Therapy* 3:269–273.

* cited by examiner

MICROSPHERES CONTAINING CONDENSED POLYANIONIC BIOACTIVE AGENTS AND METHODS FOR THEIR PRODUCTION

1. FIELD OF THE INVENTION

The subject invention is in the field of sustained drug delivery using micro-encapsulation of bioactive agents. In particular, the invention describes improved methods for incorporating polyanionic bioactive agents into polymeric microspheres and/or nanospheres through the use of a condensing agent, as well as microspheres and/or nanospheres prepared by the method.

2. BACKGROUND OF THE INVENTION

2.1. Gene Therapy

Gene therapy was originally conceived as a specific gene replacement therapy for correcting heritable defects by delivering functionally active therapeutic genes into targeted cells. Initial efforts toward somatic gene therapy have largely relied on indirect means of introducing genes into tissues, called ex vivo gene therapy. In ex vivo protocols, target cells are removed from the body, transfected or infected in vitro with vectors carrying recombinant genes, and re-implanted into the body ("autologous cell transfer"). A variety of transfection techniques are currently available and used to transfer DNA in vitro into cells, including calcium phosphate-DNA precipitation, DEAE-Dextran transfection, electroporation, liposome mediated DNA transfer, and transduction with recombinant viral vectors. Such ex vivo treatment protocols have been proposed to transfer DNA into a variety of different cell types including epithelial cells (Morgan et al., U.S. Pat. No. 4,868,116; Morgan & Mulligan, WO87/00201; Morgan et al., 1987, *Science* 237:1476–1479; Morgan & Mulligan, U.S. Pat. No. 4,980,286), endothelial cells (WO89/05345), hepatocytes (Wilson & Mulligan, WO89/07136; Wolff et al., 1987, *Proc. Natl. Acad. Sci. USA* 84:3344–3348; Ledley et al., 1987, *Proc. Natl. Acad. Sci. USA* 84:5335–5339; Wilson et al., 1990, *Proc. Natl. Acad. Sci. USA* 87:8437–8441), fibroblasts (Palmer et al., 1987, *Proc. Natl. Acad. Sci. USA* 84:1055–1059; Anson et al., 1987, *Mol. Biol. Med.* 4:11–20; Rosenberg et al., 1988, *Science* 242:1575–1578; Naughton & Naughton, U.S. Pat. No. 4,963,489), lymphocytes (Anderson et al., U.S. Pat. No. 5,399,346; Blaese et al., 1995, *Science* 270:475–480) and hematopoietic stem cells (Lim et al., 1989, *Proc. Natl. Acad. Sci. USA* 86:8892–8896; Anderson et al., U.S. Pat. No. 5,399,346).

Direct in vivo gene transfer has recently been attempted with formulations of DNA trapped in liposomes (Ledley et al., 1987, *J. Pediatrics* 110:1), in proteoliposomes that contain viral envelope receptor proteins (Nicolau et al., 1983, *Proc. Natl. Acad. Sci. USA* 80:1068), and with DNA coupled to a polylysine-glycoprotein carrier complex. In addition, "gene guns" have been used for gene delivery into cells (Australian Patent No. 9068389). Some have even speculated that naked DNA, or DNA associated with liposomes, can be formulated in liquid carrier solutions suitable for injection into interstitial spaces for transfer of DNA into cells (Felgner, WO90/11092).

Perhaps one of the greatest problems associated with currently devised gene therapies, whether ex vivo or in vivo, is the inability to transfer DNA efficiently into a targeted cell population and to achieve high level expression of the gene product in vivo. Viral vectors are regarded as the most efficient system, and recombinant, replication-defective viral vectors have been used to transduce (via infection) cells both ex vivo and in vivo. Such vectors have included retroviral, adenoviral and adeno-associated, and herpes viral vectors. While highly efficient at gene transfer, the major disadvantages associated with the use of viral vectors include the inability of many viral vectors to infect non-dividing cells; problems associated with insertional mutagenesis; inflammatory reactions to the virus and potential helper virus production; antibody responses to the viral coats; and the potential for production and transmission of harmful virus to other human patients.

The efficiency of gene transfer into cells directly influences the resultant gene expression levels. In addition to the general low efficiency with which most cell types take up and express foreign DNA, many targeted cell populations are found in very low numbers in the body, so that the low efficiency of presentation of DNA to the specific targeted cell types further diminished the overall efficiency of gene transfer.

In many approaches aimed at increasing the efficiency of gene transfer into cells, the nucleic acid is typically complexed with carriers that facilitate the transfer of the DNA across the cell membrane for delivery to the nucleus. The carrier molecules bind and condense DNA into small particles which facilitate DNA entry into cells through endocytosis or pinocytosis. In addition, the carrier molecules act as scaffolds to which ligands may be attached in order to achieve site- or cell-specific targeting of DNA.

The most common DNA condensing agents used in the development of nonviral gene delivery systems include polylysine (Laemmli, 1975, *Proc. Natl. Acad. Sci. USA* 72:4288–92; Wolfert & Seymour, 1996, *Gene Therapy* 3:269–73) and low molecular weight glycopeptides (Wadhwa et al., 1995, *Bioconjugate Chemistry* 6:283–291). Polylysine amino groups have been derivatized with transferrin, glycoconjugates, folate, lectins, antibodies, or other proteins to provide specificity in cell recognition, without compromising the polylysine's binding affinity for DNA.

Clearly, improved methods of gene delivery are needed. Such methods should be amenable to use with virtually any gene of interest and should permit the introduction of genetic material into a variety of cells and tissues.

2.2. Receptor-Mediated Gene Delivery

Receptor-mediated gene delivery has emerged as a potentially useful approach for introduction of DNA into cells in vivo. An advantage of this gene delivery method is the ability to target DNA to specific tissue or cell types based on the recognition of ligands by unique receptors expressed on the cell surface (Wu et al., 1988, *J. Biol. Chem.* 263:14621–14624; Christiano et al., 1993, *Proc. Natl. Acad. Sci. USA* 90:2122-2126; Huckett et al., 1990, *Biochem. Phannacol.* 40:253–263; Perales et al., 1994, *Eur. J. Biochem.* 226:255–266). In addition, this particular delivery system is not limited by the size of the DNA and the system does not involve the use of infectious agents.

Receptor-mediated gene transfer has considerable potential for use in human gene therapy if the method can be developed to a point where it is both a reliable and efficient approach for delivery in targeted host cells. The major shortcomings of currently available techniques are transient, variable and low level expression of the transferred DNA. Any method designed to increase the efficiency of transfer of DNA into the cell will facilitate the successful development of receptor-mediated gene delivery protocols.

2.3. Microspheres and Nanospheres

Oftentimes, it is desirable to deliver pharmaceutical or other bioactive agents intracellularly rather than, or in addition to, extracellularly. Such applications are particularly useful where, for example, the bioactive agent cannot easily penetrate or traverse the cellular membrane. Examples of such bioactive agents include oligonucleotides such as antisense DNA and RNA, ribozymes, DNA for gene therapy, transcription factors, growth factor binding proteins, signalling receptors and the like. Also desirable is sustaining this delivery of bioactive agents over an extended period of time.

Microspheres and/or nanospheres are a widely used vehicle for delivering drugs intracellularly, and for sustaining the delivery for an extended time. Generally, microspheres and/or nanospheres comprise a biocompatible biodegradable polymeric core having a bioactive agent incorporated therein. Microspheres are typically spherical and have an average diameter of about 1 to 900 $\mu$m, while nanospheres are typically spherical and have an average diameter of less than 1 $\mu$m, usually less than about 300 nm.

Advantages of microsphere and/or nanosphere (hereinafter collectively "microsphere") bioactive formulations include their ability to enter cells and penetrate intracellular junctions. Another advantage of microspheres is their ability to provide sustained or controlled release of bioactive agents. Thus, microspheres provide a means for intracellular as well as extracellular controlled or sustained delivery of pharmaceutical and other bioactive agents.

Often, the pharmaceutical or bioactive agent is a polyionic molecule. These polyionic molecules often do not pack well into microspheres and thus have reduced incorporation efficiencies. Examples of polyanionic bioactive agents include nucleic acids, for example DNA and RNA; many proteins, for example bone acidic glycoprotein 75,000 da (BAG75) and other phosphoproteins of bones and teeth, $\beta$-lactoglobulin, and phycocyanin; and glycosaminoglycans, for example heparin, heparan sulfate, chondroitin sulfate, polyuronic acid, and hyaluronic acid. In particular, DNA is a highly desirable polyanionic bioactive agent for delivery via microspheres.

However, efforts to formulate DNA within microspheres have been hampered by several difficulties. For example, present methods exhibit very low efficiencies of incorporation—most of the DNA present in the emulsion used to prepare the microspheres does not get into the microspheres. Methods that enhance the efficiency of DNA incorporation would have the beneficial effect of requiring less starting DNA to produce an end product with a given amount of incorporated DNA. Such methods might also increase the amount of DNA incorporated into each microsphere, allowing the introduction of fewer microspheres into the treatment site to deliver a given amount of total DNA to a patient.

Moreover, incorporation of DNA into microspheres is plagued by fragmentation of the DNA. In one common method, DNA microspheres are formed using a water-in-oil-in-water double emulsion method. Unfortunately, each of the two emulsifying steps frequently involves sonication, which causes fragmentation of the DNA.

Having available methods for increasing the efficiency of incorporating DNA within microspheres without inducing DNA fragmentation would be extremely advantageous. Such DNA-containing microspheres would facilitate intracellular as well as extracellular controlled or sustained release of therapeutic DNA agents at the site of medical intervention. These microspheres would be particularly advantageous for delivering DNA for use in gene therapy.

An alternative method for intracellular delivery is liposomes. However, liposomes, including polycationic liposomes, do not have the desirable sustained release properties that microspheres exhibit, as they tend to be less stable and to release their contents rapidly. Thus, for many purposes, lipsomal delivery systems are not as effective as microsphere delivery systems. Furthermore, liposomes are made using completely different methods from those used to make microspheres.

3. SUMMARY OF THE INVENTION

Many advantages are provided by the present invention, which in one aspect is directed to a method of making microspheres containing polyanionic bioactive agents. The efficiency of incorporation of the polyanionic bioactive agents into the microspheres is increased by using a condensing agent to condense the polyanionic bioactive agent during the manufacture of the microsphere.

In its broadest sense, the method involves the use of a condensing agent in one of the phases used to produce the microsphere. Many methods for making microspheres, which are known in the art, are amenable to the use of the condensing agent as described herein. These methods include, but are not limited to, water-in-oil-in-water (W/O/W) double emulsions, water-in-oil (W/O) or oil-in-water (O/W) single emulsions, salting out, diafiltration, coacervation, hot melt, and spray drying. A preferred method for use in conjunction with a condensing agent is the water-in-oil-in-water double emulsion method.

In one illustrative embodiment of the invention, microspheres containing polyanionic bioactive agents are prepared using a water-in-oil-in-water double emulsion method, which method comprises the steps of: (a) dissolving at least one polymer in a water-immiscible organic solvent to yield an organic phase; (b) dissolving a polyanionic bioactive agent in aqueous solution to yield a first aqueous phase; (c) emulsifying the organic and first aqueous phases to yield a first milky emulsion; (d) dissolving a condensing agent in aqueous solution to yield a second aqueous phase; (e) emulsifying the first milky emulsion and the second aqueous phase to yield a second milky emulsion; and (f) removing the organic solvent from the second milky emulsion to yield microspheres containing condensed polyanionic bioactive agent. The removal of the organic solvent in the final step is preferably by means of evaporation.

In a preferred embodiment, the polymer is a biocompatible biodegradable polymer, such as polylactic polyglycolic acid (PLGA). Preferred water-immiscible organic solvents include chloroform and methylene dichloride. In an alternative preferred embodiment, the second aqueous phase may optionally include an emulsifying agent; this emulsifying agent is preferably polyvinyl alcohol (PVA).

Many polyanionic bioactive agents are useful in the present invention, including nucleic acids, such as DNA, RNA, or oligonucleotides; proteins, such as bone acidic glycoprotein 75,000 da (BAG75) and other phosphoproteins of bones and teeth, and $\beta$-lactoglobulin; and glycosaminoglycans, such as polyuronic acid and hyaluronic acid. In a preferred embodiment, the polyanionic bioactive agent is a nucleic acid, particularly DNA. For the condensing agent, a preferred embodiment is a polycation, preferably polylysine, especially poly-L-lysine, and derivatives thereof. Alternatively, the polycation may also preferably be a polypeptide, for example myelin basic protein, histones, DNA binding domains from histones, DNA binding domains from, for example, transcription factors, and synthetic polypeptides made up of one or more of these domains.

In another aspect, the present invention is directed to microspheres containing polyanionic bioactive agents. Generally, the microspheres comprise a polymeric core, preferably a biocompatible biodegradable polymeric core, and have entrapped, entrained, embedded, encapsulated, or otherwise incorporated therein a condensed polyanionic bioactive agent. Thus, in one illustrative embodiment, the microspheres comprise a polymer, preferably a biocompatible biodegradable polymer, a condensing agent, and a polyanionic bioactive agent. In preferred embodiments, the polyanionic bioactive agent is a nucleic acid, particularly DNA, as described above. Similarly, as described above, preferred condensing agents are polycations, particularly polylysine and derivatives thereof. A preferred biocompatible biodegradable polymer is polylactic polyglycolic acid.

4. DETAILED DESCRIPTION OF THE INVENTION

4.1. Introduction

The present invention describes compositions and methods relating to improved microspheres for the delivery of polyanionic bioactive agents. For the purposes of this Application, the terms "microsphere" and "microspheres" are to be taken as encompassing both microspheres and nanospheres, except where specifically noted. The terms should also be read expansively to incorporate such similar expressions as "microparticle" and "nanoparticle", and other related concepts.

Microspheres are comprised of a biocompatible biodegradable polymer and have at least one bioactive agent, for example condensed DNA, entrapped, entrained, embedded, encapsulated or otherwise incorporated therein. Microspheres typically have a diameter of less than about 900 $\mu$m, preferably less than about 300 $\mu$m, more preferably less than about 10 $\mu$m, even more preferably less than about 1 $\mu$m, still more preferably less than about 800 nm, yet more preferably less than about 500 nm, further preferably less than about 300 nm, and especially preferably between about 10 nm and about 300 nm. Typically, the microspheres comprise about 0.001% to about 30% (w/w) bioactive agent, preferably about 1% to about 15% (w/w) bioactive agent.

The improved microspheres of the present invention achieve increased encapsulation efficiencies, increased resistance of the bioactive agent to sonication damage, and improved release properties through condensation of the polyanionic bioactive agent during the production of the microspheres. The condensation may be carried out with the use of a condensing agent, particularly a polycationic agent. While not intending to be bound by any particular theory, it is believed that such a condensing agent binds to the negatively charged polyanionic bioactive agent and results in extensive compaction and concomitant increased incorporation of the bioactive agent into the microspheres.

The invention is based, in part, on the discovery that adding a polycationic condensing agent to a polyanionic bioactive agent during the production of microspheres increases the efficiency with which the bioactive agent is incorporated into the microspheres. With respect to one particular polyanionic bioactive agent, DNA, it was additionally discovered that particles of condensed DNA are strongly protected from shear-induced sonication effects. Such protection is important for successful encapsulation of intact DNA into microspheres, as some versions of this process require multiple sonication steps.

In one embodiment of the invention condensed DNA may be incorporated into polylactic-polyglycolic acid (PLGA) microspheres and used for delivery of DNA into targeted host cells. Such microspheres comprise a biodegradable polymeric core having a nucleic acid incorporated therein.

In a further embodiment of the invention, the microspheres containing condensed polyanionic bioactive agents may be further incorporated into any biocompatible matrix material. Such materials may include, but are not limited to biodegradable or non-biodegradable materials that support all attachment and growth, powders or gels. Materials may be derived from synthetic polymers or naturally occurring proteins such as collagen, other extracellular matrix proteins, or other structural macromolecules.

In an embodiment of the invention, the methods of the invention may be used to prepare a drug delivery system for transfer of nucleic acids, especially DNA, into targeted host cells. The DNA to be used in the practice of the invention may include DNA encoding translational products (i.e., proteins) or transcriptional products (i.e., antisense or ribozymes) that act as therapeutic agents for treatment of wounds and diseases. For example, the DNA may comprise genes encoding therapeutically useful proteins such as growth factors, cytokines, hormones, etc. Additionally, the DNA may encode antisense or ribozyme molecules that may inhibit the translation of mRNAs encoding proteins that, for example, inhibit wound healing, induce inflammation or cause disease.

4.2. Basic Microsphere Preparation

The present invention was developed in conjunction with the water-in-oil-in-water double emulsion protocol for encapsulating charged bioactive agents, but the polyanionic bioactive agent condensation method can also be adapted for use with many other protocols that have been used to prepare microspheres. The water-in-oil-in-water double emulsion protocol is described in Levy et al., WO96/20698; Yamamoto et al., European Patent Application EP 190,833; and Okada et. al., U.S. Pat. No. 5,480,656, the disclosures of which are hereby incorporated by reference in their entireties. A brief description of this protocol is provided here; it will be discussed in more detail infra.

In the standard embodiment of the water-in-oil-in-water double emulsion protocol for making microspheres containing hydrophilic bioactive agents (including polyanionic bioactive agents), at least one biocompatible biodegradable polymer is dissolved in a water-immiscible organic solvent to yield an organic phase. The hydrophilic bioactive agent is dissolved in water to yield a first aqueous phase, and the two phases are then emulsified to yield a water-in-oil (W/O) emulsion. A second aqueous phase is then formed, optionally including an emulsifying agent that facilitates the formation of an emulsion. The W/O emulsion and the second aqueous phase are again emulsified to yield a double water-in-oil-in-water (W/O/W) emulsion. The organic solvent is then removed from the W/O/W emulsion, yielding microspheres containing the hydrophilic bioactive agent. The microspheres are recovered by ultracentrifugation.

4.3. Condensation Improvement Rationale

The standard double emulsion protocol is effective for producing microspheres containing polyanionic bioactive agents, but it suffers from several drawbacks. One of the most important of these is that it has a relatively low percentage of incorporation of bioactive agent. For example, when used with DNA, as little as 10% of the DNA is incorporated into the microspheres. The remaining 90% is transferred into the second aqueous phase. While not intending to be bound by any particular theory, it is believed that the poor efficiency of incorporation is caused in part by charge-charge repulsions between molecules of bioactive agent, which prevent them from packing into the microspheres. Methods that improve the efficiency of bioactive agent incorporation would have the beneficial effect of requiring less starting bioactive agent material to produce an end product with a given amount of incorporated bioactive agent. They might also have the effect of increasing the amount of bioactive agent available per microsphere, and thus reduce the number of microspheres that were needed to provide a given dose of bioactive agent to a patient.

Another drawback of the double emulsion protocol, particularly when used to encapsulate nucleic acids and especially to encapsulate long DNA molecules such as plasmids and chromosomal DNA, is that each of the two emulsifying steps often involves a sonication step, which results in fragmentation of the nucleic acid. This fragmentation is somewhat reduced with supercoiled DNA, but it is still present at a level that presents problems with long DNAs. Mathiowitz et al., WO95/24929 (Example 5, pages 29–31). The sonication is generally used to produce microspheres of nanosphere size, which may not be formed in the absence of sonication. Accordingly, having available methods for increasing the efficiency of formulating nucleic acids into microspheres without fragmentation of the nucleic acid would be extremely advantageous, and would facilitate the production of extremely small microspheres containing intact nucleic acid.

The release properties of the microspheres is another potential area for improvement. Present microsphere formulations hold their contents quite well in storage, but once they are introduced into the extracellular fluids they begin to release the bioactive agent. Methods that allowed the release to be delayed until the microsphere was taken up by a cell and to be sustained over a longer period of time would be of great value for many applications, such as sustained delivery of DNA in gene therapy protocols.

All of these aspects of microspheres can be improved with the use of an agent that condenses the polyanionic bioactive agent. Condensation has the effect of increasing the amount of polyanionic bioactive agent that can be incorporated into the microspheres. Microspheres containing DNA have the DNA distributed throughout the bulk of the microsphere (not merely on the surface), and condensing the DNA permits a much higher loading capacity. Similarly, condensation also has the potential to reduce the size of the microspheres. More importantly, the condensation dramatically reduces the amount of bioactive agent remaining in the second aqueous phase, to essentially undetectable levels, and correspondingly increases the amount of bioactive agent incorporated into the microspheres. Without intending to be limited to any particular theory, it is believed that the condensing agent is drawn into the organic phase, where its charge holds the bioactive agent, thus making the bioactive agent more readily available for incorporation into the microspheres. The condensation therefore dramatically increases the efficiency of incorporation of bioactive agent into the microspheres and thus has the potential to greatly reduce the cost of manufacturing bioactive agent microspheres. Using the methods of the invention has the potential to increase the efficiency by which polyanionic bioactive agents are incorporated into microspheres by as much as 80% or 90%, or even 95% or more. For nucleic acid bioactive agents, efficiency increases on the order of 90% to 95% are typical.

Condensation also protects nucleic acids from fragmentation caused by sonication. Without intending to be bound by any mechanism of action, it is believed that the condensation of the DNA into a more compact form serves to protect it from the shear forces created during sonication. The protection permits the use of sonication during production and facilitates the production of smaller microspheres. Furthermore, condensation also protects nucleic acids from nuclease destruction in vivo.

Finally, condensation changes the release properties of the microspheres. At physiological pH (7.4), the bioactive agent is bound to the condensing agent within the microsphere and is not released into the extracellular fluids. Only after the microsphere is taken up by the cell will the condensate be disrupted and the bioactive agent made available to the cell. Without intending to be bound by any method of action, the ability of the microspheres produce a sustained release of their contents is believed to be related to the entrapment of the bioactive agent within the structure of the microspheres themselves, coupled with the tight interaction between the condensing agent and the bioactive agent. Thus, microspheres in which the bioactive agent, in an uncondensed form, was merely bound to the outside of the microsphere would not be expected to have the favorable sustained release properties of the microspheres of the present invention.

4.4. Microsphere Preparation by the Double Emulsion Method

As discussed supra, in a preferred embodiment the microspheres of the present invention are formed by the water-in-oil-in-water double emulsion protocol, described in Levy et al., WO96/20698; Yamamoto et al., European Patent Application EP 190,833; and Okada et. al., U.S. Pat. No. 5,480,656.

In the standard embodiment of the water-in-oil-in-water double emulsion protocol for making microspheres containing hydrophilic bioactive agents (including polyanionic bioactive agents), a first emulsion is formed between an organic phase and a first aqueous phase. To form the organic phase, at least one biocompatible polymer is dissolved in a water-immiscible organic solvent. The polymer(s) is (are) typically dissolved in the organic solvent at a concentration ranging from about 20 mg/ml to about 200 mg/ml, preferably in the range of about 30 mg/ml to about 40 mg/ml, especially in the range of about 30 mg/ml to about 35 mg/ml.

The water-immiscible solvent preferably has a boiling point not higher than 120° C. Preferred water-immiscible organic solvents include halogenated alkanes, ethyl acetate, ethyl ether, benzene, toluene, etc.; particularly preferred are chloroform and methylene dichloride, especially chloroform. Because the microspheres may retain some residual solvent, in certain embodiments non-carcinogenic solvents may be preferred.

4.4.1. Polymers

A great many polymer molecules are suitable for making microspheres. Depending on the type of delivery contemplated, the polymers may be nonbiodegradable, or, preferably, biodegradable. The polymers may be natural or synthetic. Discussions and lengthy (but non-limiting) lists of suitable polymers can be found in Mathiowitz et al., WO95/24929 (particularly pages 6–9), and Goldstein et al., WO97/47254 (particularly pages 22–35, which also include descriptions of other elements of the double-emulsion protocol), the disclosures of which are hereby incorporated by reference in their entirety. Particularly preferred polymers for the present invention include biocompatible biodegradable polymers such as polylactic acid, polyglycolic acid, polycaprolactone, and co-polymers thereof. In preferred embodiments, the biocompatible biodegradable polymer is a copolymer of polylactic acid and polyglycolic acid (PLGA) having a proportion between the lactic acid/glycolic acid units ranging from about 100/0 to about 25/75. As is well known in the art (see the references cited supra), the release properties of the microspheres may be manipulated by varying the particular polymer(s) used and, when more than one polymer is used, the ratio of the different polymers.

The polymers used in producing the microspheres may optionally be constructed of multiple subunits. The resulting subunits are referred to as "multiblock copolymers." This multiblock method may be used to facilitate easier production of the microspheres, or to improve various properties of the microspheres themselves. For example, an emulsifying agent may be incorporated into the polymer subunits, obviating the need for such an agent during the production of the microspheres and thereby simplifying the protocol. Alternatively, hydrophobic or hydrophilic subunit blocks may be used to facilitate the incorporation of a wider variety of bioactive agents than are normally amenable to encapsulation in microspheres. Suitable multiblock copolymers, as well as their uses, are described in Levy et al., WO96/20698, and Goldstein et al., WO97/47254, the disclosures of which are hereby incorporated by reference.

The polymers used in producing the microspheres may optionally have other molecules bound to them. These modifications may, for example, impart the microspheres with the ability to target and bind specific tissues or cells, allow them be retained at the administration site, protect incorporated bioactive agents, exhibit antithrombogenic effects, prevent aggregation, and/or alter the release properties of the microspheres. Production of such modified polymers and surface-modified microspheres made from them are discussed in Levy et al., WO96/20698, the disclosure of which is hereby incorporated by reference. The targeting agent may alternatively be bound to a polycationic condensing agent, as discussed in section 4.5.1.5, infra.

As a specific example, it may be desirable to incorporate receptor-specific molecules, such as for example antibodies, into the microspheres to mediate receptor-specific particle uptake. Agents and methods for imparting microspheres with these and additional desirable properties are well known in the art (see, e.g., Troster et al., 1990, *Intl. J. Pharmaceutics* 61:85–100; Davis et al., 1993, *J. Controlled Release* 24:157–163; Muller et al., 1993, *Intl. J. Pharmaceutics* 89:25–31; Maruyama et al., 1994, *Biomaterials* 15:1035–1042; Leroux et al., 1994, *J. Biomed. Materials Res.* 28:471–481). Any of these methods may be used in conjunction with the present invention.

4.4.2. Polyanionic Bioactive Agents

The first aqueous phase is formed by dissolving a hydrophilic bioactive agent in water to yield an aqueous phase. In the present invention, the hydrophilic bioactive agent is a polyanionic bioactive agent. The condensation step of the present invention increases the efficiency of incorporation of the polyanionic bioactive agent into the microspheres, thus allowing the use of less agent in the preparation. The concentration of polyanionic bioactive agent used to form the aqueous phase is typically in the range of about 0.10 mg/ml to about 20 mg/ml, preferably in the range about 2 mg/ml to about 8 mg/ml, especially in the range about 4 mg/ml to about 6 mg/ml.

The present invention is useful for preparations of a wide variety of polyanionic bioactive agents. The agents described infra primarily exert their bioactive effect by causing direct changes to the cell. However, the term "bioactive" as used in this Application is intended to include any substance that interacts with biological elements. Thus, bioactive agents include substances such as dyes or labelling proteins whose primary use is to facilitate identification or visualization of biological structures or functions.

4.4.2.1. Nucleic Acids

The most important polyanionic bioactive agents contemplated by the present invention are the nucleic acids. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, *J. Biol. Chem.* 272:6479–89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), dimethylene-sulfoxide ($-CH_2-SO-CH_2-$), dimethylene-sulfone ($-CH_2-SO_2-CH_2-$), 2'-O-alkyl, and 2'-deoxy-2'-fluoro phosphorothioate internucleoside linkages are well known in the art (see Uhlmann et al., 1990, *Chem. Rev.* 90:543–584; Schneider et al., 1990, *Tetrahedron Lett.* 31:335 and references cited therein).

The nucleic acids may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

The nucleic acid itself may act as a therapeutic agent, such as for example an antisense DNA that inhibits MRNA translation, or the nucleic acid may encode a variety of therapeutic transcription or translation products that will be expressed by the target cells. Useful transcription products include antisense RNAs, ribozymes, viral fragments and the like. Useful translation products include proteins, such as, for example, membrane proteins, transcription factors, intracellular proteins, cytokine binding proteins, and the like.

In a preferred embodiment of the invention, the nucleic acid is a DNA molecule that encodes gene products that stimulate or promote healing of wounded or damaged tissues in vivo or alleviate the symptoms of disease. Particularly preferred are therapeutic proteins, such as growth factors and hormones. Particularly preferred growth factors are transforming growth factor-beta (TGF-β), fibroblast growth factor (FGF), platelet derived growth factor (PDGF), insulin like growth factor (IGF), and bone morphogenic factor (BMP); particularly preferred hormones are growth hormone (GH) and human parathyroid hormone (PTH).

Modified gene sequences, i.e. genes having sequences that differ from the gene sequences encoding the native proteins, are also encompassed by the invention, so long as the modified gene still encodes a protein that functions to stimulate healing in any direct or indirect manner. These modified gene sequences include modifications caused by point mutations, modifications due to the degeneracies of the genetic code or naturally occurring allelic variants, and further modifications that have been introduced by genetic engineering, i.e., by the hand of man, to produce recombinant nucleic acid molecules.

The DNA encoding the transcription or translation products of interest may be recombinantly engineered into a variety of host vector systems that provide for replication of the DNA in large scale for the preparation of condensed DNA microspheres. These vectors can be designed to contain the necessary elements for directing the transcription and/or translation of the DNA sequence contained in the microsphere. Methods which are well known to those skilled in the art can be used to construct expression vectors having the protein coding sequence operatively associated with appropriate transcriptional/translational control signals. These methods include in vitro recombinant DNA techniques and synthetic techniques. See, for example, the techniques described in Sambrook et al., 1992, MOLECULAR CLONING: A LABORATORY MANUAL (Cold Spring Harbor Laboratory, New York); and Ausubel et al., 1989, CURRENT PROTOCOLS IN MOLECULAR BIOLOGY (Greene Publishing Associates & Wiley Interscience, New York), the contents of both of which are hereby incorporated by reference.

The genes encoding the proteins of interest may be operatively associated with a variety of different promoter/enhancer elements. The promoter/enhancer elements may be selected to optimize for the expression of therapeutic amounts of protein. In some instances, the promoter elements may be constitutive or inducible promoters and can be used under the appropriate conditions to direct high level or regulated expression of the gene of interest.

It is also within the scope of the invention that multiple genes, combined on a single genetic construct under control of one or more promoters, or prepared as separate constructs of the same or different types, may be used. Thus, an almost endless combination of different genes and genetic constructs may be employed. Any and all such combinations are intended to fall within the scope of the present invention.

4.4.2.2. Other Polyanionic Molecules

Other polyanionic bioactive agents are also suited for use in the present invention. Examples of polyanionic bioactive agents include many proteins, for example bone acidic glycoprotein 75,000 da (BAG75) and other phosphoproteins of bones and teeth, β-lactoglobulin, and phycocyanin; and glycosaminoglycans, for example heparin, heparan sulfate, chondroitin sulfate, polyuronic acid, and hyaluronic acid. The present invention is useful for delivery of any desired bioactive or other agent having a net negative charge per molecule of at least about $-5$ to about $-10$ at physiological pH. Alternatively, the charge on the polyanionic bioactive agent may be expressed in terms of $\zeta$-potential. The polyanionic bioactive agent preferably has a $\zeta$-potential of at least about $-5$ mV to about $-10$ mV, more preferably at least about $-20$ mV to about $-25$ mV.

The first aqueous phase may optionally contain other components. For example, it may contain a drug-retaining substance, such gelatin or agar. The first aqueous phase may also contain an agent for adjusting the pH of the phase and/or a stabilization agent. It may also include any other substances that do not substantially interfere with the production of the microspheres.

The organic phase and the first aqueous phase are then emulsified. This emulsification is preferably performed by dropwise addition of the first aqueous phase to the organic phase followed by rapid vortexing, but alternatively may be done by sonication, homogenization, or other mechanical method. Indeed, as discussed supra, one of the advantages of the condensation method is that the bioactive agent, especially DNA, is protected from sonication-induced damage, improving the results when sonication is used as an emulsification method. The resulting water-in-oil (W/O) emulsion has a distinct milky appearance.

A second aqueous phase is then formed. The second aqueous phase may optionally include an emulsifying agent that facilitates the formation of an emulsion. Preferred emulsifying agents include ionic surfactants (e.g. sodium lauryl sulfate), non-ionic surfactants (e.g. the polyoxyethylenesorbitans, commonly sold under the name TWEEN), polyvinyl pyrrolidone, lecithin, or gelatin; particularly preferred is polyvinyl alcohol (PVA). The emulsifying agent is preferably in the range of about 0.01% to about 20% by weight of the volume of the second aqueous phase, particularly preferably about 0.05% to about 10%.

The W/O emulsion and the second aqueous phase are then emulsified to yield a multiple water-in-oil-in-water (W/O/W) emulsion. This emulsification is preferably performed by homogenization by high-speed stirring, preferably at 4° C. and 30,000 rpm in a homogenizer (e.g. an Omni GLH Homogenizer), but alternatively may be done by sonication, vortexing, or other mechanical method. The resulting W/O/W emulsion again has a distinct milky appearance.

The organic solvent is removed from the multiple W/O/W emulsion (preferably by evaporation while stirring, particularly stirring overnight at 4° C., optionally under reduced pressure), yielding microspheres containing the hydrophilic bioactive agent. The microspheres may be recovered by ultracentrifugation (e.g. 25,000 rpm at 4° C. for 20 min), optionally washed one or more times with water, Tris-EDTA (TE), or other suitable buffer, and optionally resuspended in water or other suitable buffer, frozen (e.g. on dry ice for 30 min), and lyophilized. The lyophilized microspheres may be stored in a desiccator at, for example, 4° C.

4.5. Condensation

In the present invention, the standard double emulsion protocol includes an agent for condensing the polyanionic bioactive agent.

4.5.1. SUITABLE CONDENSING AGENTS

The ability of an agent to condense DNA and its effective amounts may be assayed by any of the methods known in the art. For example, condensation may be measured by comparing the kinetics in solution of condensed DNA and uncondensed DNA, and then further comparing the kinetics in the presence of a surfactant, such as a detergent. It may also be measured by changes in the surface ζ-potential of the DNA in solution (Wolfert et al., 1996, *Human Gene Therapy* 7:2123–33), or by viewing the DNA with an electron microscope (Laemmli, 1975, *Proc. Natl. Acad. Sci. USA* 72:4288–92) or atomic force microscope (Wolfert & Seymour, 1996, *Gene Therapy* 3:269–73). All of these cited references are hereby incorporated by reference.

Most agents suitable for use as condensing agents for polyanionic bioactive agents are polycations. The term "polycations", as used in this application, generally refers to molecules with more than one positive charge, but may also include certain monovalent cations that, because of their size or for some other reason, are able to condense polyanionic bioactive agents such as DNA. Such monovalent cations are intended to be within the scope of this application. For general discussion of DNA condensation with polycations, including a non-limiting list of some suitable condensing agents, see Lasic, 1997, LIPOSOMES IN GENE DELIVERY (CRC Press, Boca Raton, Fla.), especially pages 33–37 and 56–61, the disclosure of which is hereby incorporated by reference.

4.5.1.1. Polylysine

One preferred family of condensing agents is the polylysines. Polylysines consist of chains of varying lengths of positively charged lysine residues. These lysine residues can be either in the D or L configuration, or a mixture of the two enantiomers; poly-L-lysine is preferred. For experiments demonstrating the use of polylysine as a DNA condensing agent, see Laemmli, 1975, *Proc. Natl. Acad. Sci. USA* 72:4288–92 and Wolfert & Seymour, 1996, *Gene Therapy* 3:269–73, the disclosures of which are hereby incorporated by reference. As used in this application, the term "polylysine" is meant to include any variants of polylysine, regardless of length, structure, or modification, that are capable of condensing DNA or other polyanionic bioactive agents. These modifications may include methylation (Bello et al., 1985, *J. Biomol. Struct. Dyn.* 2:899–913) or glycosylation (Martinez-Fong et al., 1994, Hepatology 20:1602–08), and may be made before or after synthesis of the polylysine.

4.5.1.2. Other Polypeptides

In an alternative embodiment, the condensing agent is a polycationic polypeptide. Several amino acids are known to be positively charged at physiological pH. Among the naturally occurring, genetically encoded amino acids, lysine, arginine, and histidine are positively charged. Other, naturally occurring non-genetically-encoded amino acids and synthetic amino acids may also be positively charged, as may be other naturally occurring, genetically encoded amino acids under certain conditions. These amino acids can be polymerized into chains, resulting in polycationic polypeptides, which are excellent condensing agents (indeed, polylysine is one specific member of the family of polycationic polypeptides). These polycationic polypeptides may be either naturally occurring or synthetic, and synthetic polypeptides may be produced by either chemical synthesis or recombinant methods. They may be either homopolymers, such as polylysine, polyarginine, polyornithine, or polyhistidine, or heteropolymers, such as proteins such as myelin basic protein.

One particularly useful group of polypeptides is the group of DNA binding proteins. These proteins may either bind DNA non-specifically, such as histones or sperm surface proteins (Lavitrano et al., 1992, *Mol. Reprod. Dev.* 31:161–69), or specifically, such as transcription factors. These proteins may be used either as whole proteins or as peptide fragments that include the DNA binding domains. They may also be made synthetically, either as individual proteins or domains or as longer peptides consisting of repeating domains from one protein or varying or repeating domains from several different proteins. Many other naturally occurring polypeptides and proteins are polycationic as well.

All of these natural and synthetic polypeptides and proteins are acceptable condensing agents for use in the present invention. As non-limiting examples, Wadhwa et al., 1995, *Bioconjugate Chemistry* 6:283–291 has used low molecular weight glycopeptides as DNA condensing agents; Niidome et al., 1997, *J. Biol. Chem.* 272:15307–12 has used cationic amphiphilic alpha-helical oligopeptides with repeating sequences as DNA condensing agents; and Chen et al., 1994, *Human Gene Therapy* 5:429–35 has used galactosylated histones for gene delivery.

One skilled in the art will recognize that variants of all these different protein structures would also be expected to function as condensing agents. Such a skilled artisan would recognize the possibility of making conservative substitutions in the polypeptides that would not disturb the function as a condensing agent, including substitution with non-genetically-encoded amino acids and/or D-enantiomers of genetically encoded as well as non-genetically-encoded amino acids. Indeed, virtually any polypeptide that is polycationic in nature is likely to function as a condensing agent, and the skilled artisan could ascertain the degree of condensing ability with routine experimentation. All synthetic and natural polycationic polypeptides that condense DNA or other polyanionic bioactive agents are intended to be included in the category of "condensing agents" useful in the present invention.

4.5.1.3. Elemental Cations

An alternative embodiment of the polycationic condensing agent is elemental cations, particularly divalent cations such as $Mg^{2+}$ or $Ca^{2+}$ (in the form of salts, such as $MgCl_2$ or $CaCl_2$, respectively). Indeed, $Ca^{2+}$ in the form $Ca_3(PO_4)_2$ is one of the most commonly known and used agents for DNA condensation in preparation for naked DNA transfection. Other suitable elemental cations include $Co^{3+}$ (particularly in the form of cobalt hexamine, $Co(NH_3)_6^{3+}$, or cobalt pentamine), $La^{3+}$, $Al^{3+}$, $Ba^{2+}$ and $Cs^+$. These cations will generally be used in the form of a salt, particularly halide salts such as chloride and bromide salts, but also other salts.

4.5.1.4. Other Polycations

The present invention is not intended to be limited to the polycations listed above, or any other particular set of polycationic molecules. Any polycationic molecule that has the property of condensing DNA or other polyanionic bioactive agents is within the scope of the condensing agents of the present invention. Thus, for example, such commonly known polycationic DNA condensing agents as polybrene, spermine, spermidine, protamine (including protamine sulfate and other salts; see, for example, Sorgi et al., 1997, *Gene Therapy* 4:961–68), polyethyleneimine, putrescine, cadaverine, hexamine, and other polyamines, and derivatives thereof, such as partially or fully methylated versions, are all considered to be within the scope of the present invention.

Additionally, any group of two or more of the cations, from the same or different categories, may be used in any combination that effectively condenses the polyanionic bioactive agent.

4.5.1.5. Modified Polycations

The polycations may optionally have other molecules bound to them, such as, for example, a polypeptide or a linker for the attachment of a polypeptide. In particular, this polypeptide may be an agent that imparts the microspheres with the ability to target and bind specific tissues or cells, allow them be retained at the administration site, etc., as discussed for multiblock co-polymers in section 4.4.1, supra. The polypeptide may be attached, for example, by a disulfide linkage or the well known biotin-avidin system. If the condensing agent is also a polypeptide, the two molecules may also be part of the same peptide chain, bound by a standard peptide bond.

For example, it may be desirable to create hybrid molecules combining a receptor-specific molecule and the condensing agent. See, e.g., Sosnowski et al., 1996, J. Biol. Chem. 271:33647–53 (condensing agent polylysine bound to targeting agent basic fibroblast growth factor). The receptor-specific molecule may be, for example, an antibody, a hormone, a growth factor, or any other molecule imparting target specificity. These hybrid molecules are an efficient way to provide condensation and targeting in a single molecule.

4.5.2. Using Condensing Agents

The condensing agent can be added to the double emulsion protocol at any point. Preferably, it is added to one of the aqueous phases before emulsification; particularly preferably, it is added to the second aqueous phase, along with the optional emulsifying agent, such as PVA, if such emulsifying agent is used. In an alternative embodiment, the condensing agent is covalently bound to the polymer that comprises the core of the microsphere.

The condensing agent is added in an amount that is effective to condense the polyanionic bioactive agent. The effective amount will depend on the precise composition of the second emulsion. Typically, the amount to use is an amount such that molar quantity of cationic sites on the condensing agent is equal to or in excess of the molar quantity of anionic sites on the bioactive agent. The ratio of cationic sites to anionic sites is preferably between about 1 and about 20, more preferably between about 5 and about 15, and especially preferably about 10, although higher ratios are also potentially useful.

The amount of condensing agent may also be expressed in terms of the concentration ratio relative to the bioactive agent. The ratio of condensing agent:bioactive agent is preferably in the range of about 0.1:1 to about 20:1, more preferably in the range of about 0.2:1 to about 1:1, especially preferably in the range of about 0.3:1 to about 0.5:1. Alternatively, the amount of condensing agent may also be expressed in terms of the concentration ratio relative to the polymer. The ratio of condensing agent:polymer is preferably in the range of about 1:400 to about 1:20, more preferably in the range of about 1:300 to about 1:40, especially preferably in the range of about 1:200 to about 1:50. The amount of condensing agent may alternatively be expressed as a percentage of the volume of the aqueous phase in which it is dissolved; preferred percentages are in the range of about 0.1% to about 30%, more preferably about 1% to about 20%, especially about 2% to about 8%.

For using poly-L-lysine (MW 1000–4000) in the production of DNA microspheres, for example, the effective amount is preferably between about 0.1 and about 15 mg, more preferably between about 0.2 and about 5 mg, still more preferably between about 0.5 and about 2 mg, and especially preferably about 2 mg.

For using salts of elemental cations, for example $MgCl_2$ or $CaCl_2$, the effective amount is preferably between about 8 mM and about 1 M cation in the second aqueous phase, especially preferably between about 8 mM and about 0.5 mM.

4.6. Alternative Protocols

In alternative embodiments, microspheres may be prepared using protocols commonly employed in the art. These protocols include, but are not limited to, the phase-separation or coacervation protocol, described in Wantier et al., U.S. Pat. No. 5,478,564; the single-emulsion protocol, described in Jaffe, U.S. Pat. No. 4,272,398; the salting out protocol, described in Allémann et al., 1992, *Intl. J. Pharmaceutics* 87:247–253; the diafiltration method, described in Maruyama et al., 1997, Bioconjugate Chem. 8:735–42; and the hot melt, solvent removal, spray drying, double walled microsphere, and hydrogel protocols, all described in Mathiowitz et al., WO95/24929 (pages 10–13). The disclosures of the above references are hereby incorporated by reference in their entireties.

4.7. Other Aspects

4.7.1. Incorporation of Other Molecules

Optionally, the condensed bioactive agent microspheres may further include bioactive agents that facilitate particulate intracellular DNA and/or RNA processing. Such agents include, by way of example and not limitation, compounds that block or disrupt lysosomal action such as chloroquine, cytochalasin B, colchicine, polyvinyl-pyrrolidone, sucrose, and the like. Such compounds will facilitate gene transfer and entry into the cell nucleus.

4.7.2. Larger Structures

In alternative embodiments, the condensed bioactive agent microspheres may be incorporated as part of a larger structure. For example, the microspheres may be used as part of a coating for a medical device or as an element in a time-release drug delivery system, such as a capsule. See, e.g., Goldstein et al., WO97/47254, the disclosure of which is hereby incorporated by reference. In a preferred embodiment, the microspheres may be utilized in combination with a biocompatible matrix that is, for example, implanted into a patient where it releases the microspheres and their contents. Such matrix compositions function (i) to facilitate ingrowth of cells (targeting); and (ii) to harbor the microspheres (delivery). Once the microsphere-containing matrix is prepared, it is stored for future use or placed immediately in the host.

The type of matrix that may be used in the compositions, devices and methods of the invention is virtually limitless and may include both biological and synthetic matrices. The matrix will have all the features commonly associated with being "biocompatible", in that it is in a form that does not produce an adverse, allergic or other untoward reaction when administered to a mammalian host. Such matrices may be formed from both natural and synthetic materials. The matrices may be non-biodegradable in instances where it is desirable to leave permanent structures in the body, or biodegradable where the expression of the therapeutic protein is required only for a short duration of time. The matrices may take the form of sponges, implants, tubes, telfa pads, band-aids, bandages, pads, lyophilized components, gels, patches, or powders. In addition, matrices can be designed to allow for sustained release of the microspheres over prolonged periods of time. In preferred embodiments, it is contemplated that a biodegradable matrix will likely be most useful. A biodegradable matrix is generally defined as one that is capable of being reabsorbed into the body. It is to be understood that virtually any matrix polymer that is now known or that will be later developed suitable for the sustained or controlled release of nucleic acids may be employed in the present invention.

The condensed bioactive agent microsphere matrices of the invention can be transferred to the patient using a variety of techniques. Procedures for transfer of the matrices into a patient include injection into a patient at the site of the wound. Alternatively, the matrices may be surgically placed at the site of the wound either as a therapeutic implant or as a coated device.

4.7.3. Introduction Into the Patient

The condensed bioactive agent microsphere formulations of the invention can be transferred to the patient using various techniques. For example, the microspheres containing the condensed bioactive agent can be transferred directly to the host by the hand of the physician, either as a therapeutic implant or as a coated device (e.g., suture, stent, coated implant, etc.).

The examples below are provided to illustrate, not limit, the present invention.

5. EXAMPLE

Preparation and Characterization of Condensed DNA Nanospheres

5.1. General Materials and Methods

Poly-L-lysine (poly-L-lysine hydrobromide, MW 1000–4000; catalog no. P-0879, lot no. 77H5902, DP 16, MW 3400), polyvinyl alcohol (PVA) (avg. MW 30,000–70,000), and minimum essential media (MEM) were purchased from Sigma Chemicals (St. Louis, MO). 50/50 polylactic-polyglycolic acid copolymer (PLGA) (avg. MW 130,000, inherent viscosity 1.32 dL/g; catalog no. KITA, lot no. 403–01–1A) was obtained from Birmingham polymers (Birmingham, Ala.). Chloroform was purchased from Aldrich Chemical (Milwaukee, Wis.). LB media and LB agar were obtained from Boehringer Marnheim (Indianapolis, Ind.). COS-7 (ATCC CRL 1651) cells were from the American Type Culture Collection (ATCC; Rockville, Md.). Dulbecco's modified Eagle medium (DMEM), media supplements and heat inactivated "qualified" fetal bovine serum (FBS) were from Gibco BRL (Grand Island, N.Y.). Plasmid DNA was prepared by the alkaline lysis method and purified on Cesium chloride gradients. The plasmid used in the Examples is pcDNA3AlkPhos, which contains the gene encoding human placental heat-stable alkaline phosphatase inserted into the vector pcDNA3 (Invitrogen), where it is under the control of the CMV promoter; this plamid was prepared by Dr. J. Bonadio, University of Michigan.

5.2. Incorporation of Condensed DNA Into Microspheres

Condensed DNA microspheres were produced by adding the condensing agent poly-L-lysine to the second aqueous phase of the water-in-oil-in-water double emulsion protocol.

5.2.1. Materials and Methods

PLGA (90 mg) was dissolved in 3 ml chloroform. PVA (500 mg) was dissolved in 25 ml ice cold TE buffer (10 mM Tris, 0.1 mM EDTA, pH 7.3), and the solution filtered to remove undissolved particles. Poly-L-lysine solution (100 or 200 $\mu$l at 10 mg/ml (1 or 2 mg total poly-L-lysine) in TE) was mixed with the PVA solution. Marker plasmid DNA encoding human placental alkaline phosphatase (pcDNA3AlkPhos) in TE (50 $\mu$l at 10 mg/ml (0.5 mg total DNA)) was added dropwise to the PLGA solution while vortexing. The solution was emulsified by continued vortexing to form a W/O emulsion that looked very milky. The DNA-polymer emulsion was dispersed in the PVA/poly-L-lysine solution by homogenization at 4° C. and 30,000 rpm in an Omni GLH Homogenizer, yielding a W/O/W emulsion.

The W/O/W emulsion was stirred with a magnetic stirring bar at 4° C. overnight to evaporate the organic solvent. The spheres were recovered by ultracentrifugation (25,000 rpm, 4° C. for 20 min), washed three times with 25 ml TE, resuspended in 2 ml ddH$_2$O, and the resulting suspension frozen (on dry ice for 30 min) then lyophilized. The lyophilized microspheres were stored in a desiccator at 4° C.

5.2.2. Results

The addition of poly-L-lysine to the water-in-oil-in-water emulsion protocol produced microspheres of normal appearance when viewed under an electron microscope (data not shown). Scanning electron microscopy revealed a uniform spherical particle morphology with a generally smooth particle surface, and not observable debris in the preparation. Particle size was confirmed by a laser light scattering technique and ranged between 400 nm and 500 nm.

5.3. Characterization of Condensed DNA Microspheres

Condensed DNA microspheres produced as described in section 5.2 were characterized for their DNA encapsulation efficiencies and DNA release properties, as compared to microspheres containing DNA that is not condensed.

5.3.1. Materials and Methods

Microspheres were produced with the methodology detailed above in section 5.2.1, except that the poly-L-lysine was omitted from the second aqueous phase in the control microspheres. DNA content in the microspheres and in the second aqueous (PVA) phase was determined using thiazole orange as an intercalating agent and quantifying fluorescence at excitation at 500 nm and emission at 530 nm. Standard curves were constructed using the input plasmid DNA quantified using UV absorbance at 260 nm/280 nm. Dissolution studies were carried out by incubating samples of DNA-containing microspheres in an excess of TE buffer with and without 0.1% sodium dodecyl sulfate (SDS). The SDS was used to establish charge-related associations between poly-L-lysine and DNA as contributing to the DNA release and/or extraction mechanism.

5.3.2. Results

The results of the characterization are shown in Table 1. As can be seen, the addition of poly-L-lysine dramatically increased the percentage of DNA that was incorporated into the microspheres, and correspondingly decreased the amount of DNA remaining in the PVA aqueous phase, as compared to uncondensed DNA. The condensed DNA could not be released from the microspheres with TE alone, demonstrating that the condensed DNA was tightly held in the microspheres. The condensed DNA was released in the presence of 0.1% SDS, demonstrating that detergent was required to disrupt the microspheres and condensing agent to release the DNA.

TABLE 1

POLYLYSINE CONDENSED DNA - PLGA MICROSPHERES

| Sample* | Poly-L-lysine Weight (mg) | DNA in PVA Phase (%) | DNA in Microspheres, 0.1% SDS Only (%) | DNA Extracted TE only (%) | TE + 0.1% SDS (%) |
|---|---|---|---|---|---|
| Control[†] | — | 96 | n.d.[‡] | n.d. | n.d. |
| PLL1 | 1 | 0 | 26 | 1 | 44 |
| PLL2 | 2 | 0 | 83 | 2 | 104 |

*For all samples: DNA Used: pcDNA3AlkPhos; Initial DNA Weight: 0.5 mg; Polymer Weight: 90 mg; DNA Load: 0.55%
[†]Control results derived from previous experiments.
[‡]n.d.: not detectable

5.4. Transfection of Cells With Condensed DNA Microspheres

To ascertain the ability of the condensed DNA microspheres to transfer DNA to cells, the microspheres produced according to section 5.2 were used to introduce DNA encoding alkaline phosphatase into cells in a standard transfection protocol.

5.4.1. Materials and Methods

COS-7 cells were plated at $3 \times 10^5$ cells per 60 mm dish and grown to 25% confluency in DMEM supplemented with penicillin (10,000 µg/ml), L-glutamine (200 mM) and 10% FBS for 24 hours.

Transfections using marker plasmid DNA encoding heat-stable alkaline phosphatase (pcDNA3AlkPhos) were performed in DMEM (4 ml per 60 mm dish) containing 10% FBS. The COS cells were transfected with no DNA (cells only), DNA condensed by the standard calcium phosphate method, blank microspheres with prepared with 1 mg or 2 mg poly-L-lysine, or microspheres containing DNA condensed with 1 mg or 2 mg poly-L-lysine. Controls or condensed DNA microspheres (5 µg DNA/300,000 cells in DMEM) were added dropwise to triplicate wells. After 48 hours incubation at 37° C., the cells were washed with PBS, lysed, and centrifuged to collect the supernatant.

Alkaline phosphatase levels were assayed using the alkaline phosphatase detection kit from Tropix (Bedford, Mass.), following the manufacturer's protocol.

5.4.2. Results

The results of the transfection assays are shown in Table 2. The microspheres containing pcDNA3AlkPhos condensed with either 1 mg or 2 mg poly-L-lysine both demonstrated effective transfection of COS cells, at a level that was more than 10-fold greater than the background level of transfection obtained with blank microspheres or in cells only. While the transfection level was below that of the calcium phosphate standard, this reduction would be expected, since microspheres are designed to be sustained release and thus would deliver less DNA in the time frame of this simple transfection assay (see below). Thus, the condensed DNA microspheres are effective for introducing DNA into cells.

TABLE 2

TRANSFECTION RESULTS - ALKALINE PHOSPHATASE ASSAY

| Group | Light Emission |
|---|---|
| Cells only | 47.8 ± 0.3 |
| $Ca_3(PO_4)_2$ | $8.78 \times 10^7 \pm 1.03 \times 10^7$ |
| Blank microspheres (1 mg poly-L-lysine) | 50.2 ± 16.8 |
| (PLL-DNA)-PLGA microspheres (1 mg poly-L-lysine) | 560.03 ± 39.4 |
| Blank microspheres (2 mg poly-L-lysine) | 48.9 ± 15.1 |
| (PLL-DNA)-PLGA microspheres (2 mg poly-L-lysine) | 611.8 ± 102.0 |

5.5. Release of Condensed DNA From Microspheres

Because it is condensed with the poly-L-lysine and bound in the microspheres, the DNA was expected to be released slowly over time from the microspheres. The time course of release of condensed DNA from the microspheres produced according to section 5.2 was analyzed. cl 5.5.1. Materials and Methods Microspheres made of PLGA and containing DNA condensed with poly-L-lysine were produced as described in section 5.2 above. Known amounts of microspheres were resuspended in Tris-EDTA (TE) buffer (10 mM Tris, 0.1 mM EDTA, pH 7.4) or TE buffer containing 0.1% (w/v) SDS, and placed on a shaker at 37° C. The concentration of DNA released from the microspheres was determined at various times using thiazole orange as an intercalating agent and quantifying fluorescence at excitation at 500 nm and emission at 530 nm. Standard curves were constructed using the input plasmid DNA quantified using UV absorbance at 260 nm/280 nm.

5.5.2. Results

The cumulative release of DNA from the microspheres is shown in Table 3, expressed both as the total amount and as a percentage of total input. As can be seen, no DNA was released in TE buffer, which did not disrupt the microspheres. The DNA was released slowly in the presence of TE +0.1% SDS, which did disrupt the microspheres. Thus, the condensed DNA microspheres were stable under physiologic conditions, such as those found in extracellular fluids, but suitable for the sustained release of the DNA under disrupting conditions, such as those found in the interior vesicles of cells that take up the microspheres.

TABLE 3

TIMED RELEASE OF CONDENSED DNA FROM MICROSPHERES

| Time | Cumulative DNA Release in TE/SDS | | Cumulative DNA Release in TE | |
|---|---|---|---|---|
| (Days) | Total Amt* | % | Total Amt* | % |
| 0.04 | 505.19 | 48.0 | 7.91 | 0.62 |
| 0.17 | 501.73 | 48.0 | 7.91 | 0.62 |
| 0.29 | 501.73 | 47.6 | 9.12 | 0.71 |
| 2.00 | 597.30 | 56.7 | 5.40 | 0.42 |
| 3.00 | 554.02 | 52.7 | 8.99 | 0.70 |
| 7.00 | 678.67 | 64.5 | 18.71 | 1.46 |
| 10.00 | 864.27 | 82.1 | 22.02 | 1.58 |
| 13.00 | 922.44 | 87.6 | | |
| 18.00 | 948.75 | 90.1 | | |

*$\mu$g DNA/mg microspheres

EQUIVALENTS

The foregoing specification is considered to be sufficient to enable one skilled in the art to broadly practice the invention. Indeed, various modifications of the above-described means for carrying out the invention which are obvious to those skilled in the relevant arts are intended to be within the scope of the following claims. All patents, patents applications, and publications cited herein are hereby incorporated by reference in their entireties for all purposes.

What is claimed is:

1. A method for making microspheres comprising a condensed nucleic acid, said method comprising the steps of:
   (a) dissolving at least one biocompatible biodegradable polymer in a water-immiscible organic solvent to yield an organic phase;
   (b) dissolving a nucleic acid in water to yield a first aqueous phase;
   (c) emulsifying the organic and first aqueous phases to yield a first emulsion;
   (d) dissolving a condensing agent in water to yield a second aqueous phase;
   (e) emulsifying the first emulsion and the second aqueous phase to yield a second emulsion; and
   (f) removing the organic solvent from the second emulsion to yield microspheres comprising a condensed nucleic acid.

2. The method according to claim 1, wherein the nucleic acid is DNA.

3. The method according to claim 2, wherein the DNA comprises a promoter operably linked to a sequence encoding a protein.

4. The method according to claim 3, wherein the encoded protein is a therapeutic protein.

5. The method according to claim 4, wherein the therapeutic protein is a growth factor.

6. The method according to claim 5, wherein the growth factor is selected from the group consisting of transforming growth factor-beta (TGF-$\beta$), fibroblast growth factor (FGF), platelet derived growth factor (PDGF), insulin like growth factor (IGF), and bone morphogenic factor (BMP).

7. The method according to claim 4, wherein the therapeutic protein is a hormone.

8. The method according to claim 7, wherein the hormone is selected from the group consisting of growth hormone (GH) and human parathyroid hormone (PTH).

9. The method according to claim 2, wherein the DNA comprises more than one DNA molecule.

10. The method according to claim 2, wherein the DNA is viral DNA.

11. The method according to claim 10, wherein the viral DNA is adenoviral DNA.

12. The method according to claim 2, wherein the condensing agent is a polycation.

13. The method according to claim 12, wherein the polycation is polylysine.

14. The method according to claim 12, wherein the polycation is a polypeptide.

15. The method according to claim 12, wherein the biocompatible biodegradable polymer is polylactic polyglycolic acid (PLGA) and the water-immiscible organic solvent is chloroform.

16. The method according to claim 15, wherein the second aqueous phase further includes an emulsifying agent.

17. The method according to claim 16, wherein the emulsifying agent is polyvinyl alcohol (PVA).

18. A method for making microspheres comprising condensed DNA, said method comprising the steps of:
   (a) dissolving polyglycolic polylactic acid in chloroform to yield an organic phase;
   (b) dissolving DNA in water to yield a first aqueous phase;
   (c) emulsifying the organic and first aqueous phases to yield a first emulsion;
   (d) dissolving poly-L-lysine and polyvinyl alcohol in water to yield a second aqueous phase;
   (e) emulsifying the first emulsion and the second aqueous phase to yield a second emulsion; and
   (f) evaporating the organic solvent from the second emulsion to yield microspheres comprising a condensed DNA.

* * * * *